US012780804B2

(12) United States Patent
Seino et al.

(10) Patent No.: US 12,780,804 B2
(45) Date of Patent: Nov. 3, 2026

(54) FLUORINE-CONTAINING PYRIMIDINE COMPOUND AND PRODUCTION METHOD THEREFOR

(71) Applicant: UNIMATEC CO., LTD., Tokyo (JP)

(72) Inventors: Junya Seino, Kitaibaraki (JP); Rie Aotsu, Kitaibaraki (JP); Keisuke Kokin, Kitaibaraki (JP)

(73) Assignee: UNIMATEC CO., LTD. (JP)

( * ) Notice: Subject to any disclaimer, the term of this patent is extended or adjusted under 35 U.S.C. 154(b) by 1039 days.

(21) Appl. No.: 17/795,670

(22) PCT Filed: Dec. 16, 2020

(86) PCT No.: PCT/JP2020/046908

§ 371 (c)(1),
(2) Date: Jul. 27, 2022

(87) PCT Pub. No.: WO2021/161648

PCT Pub. Date: Aug. 19, 2021

(65) Prior Publication Data

US 2023/0096085 A1 Mar. 30, 2023

(30) Foreign Application Priority Data

Feb. 12, 2020 (JP) ................................ 2020-021837

(51) Int. Cl.

*C07D 403/04* (2006.01)
*C07D 401/04* (2006.01)
*C07D 405/04* (2006.01)
*C07D 417/04* (2006.01)
*C07D 471/04* (2006.01)

(52) U.S. Cl.

CPC ......... *C07D 403/04* (2013.01); *C07D 401/04* (2013.01); *C07D 405/04* (2013.01); *C07D 417/04* (2013.01); *C07D 471/04* (2013.01)

(58) Field of Classification Search

CPC .................................................... C07D 403/04
See application file for complete search history.

(56) References Cited

U.S. PATENT DOCUMENTS

| | | | |
|---|---|---|---|
| 2013/0216498 | A1 | 8/2013 | Eastwood et al. |
| 2014/0274695 | A1 | 9/2014 | Eckelbarger et al. |
| 2015/0018353 | A1 | 1/2015 | Kim et al. |
| 2015/0126366 | A1 | 5/2015 | Eckelbarger et al. |
| 2015/0126372 | A1 | 5/2015 | Eckelbarger et al. |
| 2015/0274756 | A1 | 10/2015 | Eckelbarger et al. |
| 2015/0342954 | A1 | 12/2015 | Kim et al. |
| 2016/0237059 | A1 | 8/2016 | Straub et al. |
| 2017/0050934 | A1 | 2/2017 | Morizawa et al. |
| 2017/0050957 | A1 | 2/2017 | Eckelbarger et al. |
| 2017/0342088 | A1 | 11/2017 | Shaw et al. |
| 2019/0071457 | A1 | 3/2019 | Eckelbarger et al. |
| 2019/0135793 | A1 | 5/2019 | Petrocchi et al. |
| 2019/0152989 | A1 | 5/2019 | Shaw et al. |
| 2019/0248806 | A1 | 8/2019 | Shaw et al. |
| 2019/0284207 | A1 | 9/2019 | Shaw et al. |
| 2021/0403455 | A1 | 12/2021 | Seino et al. |

FOREIGN PATENT DOCUMENTS

| | | | |
|---|---|---|---|
| CN | 1074443 | A | 7/1993 |
| CN | 102695706 | A | 9/2012 |
| CN | 104066731 | A | 9/2014 |
| CN | 105209451 | A | 12/2015 |
| EP | 3144297 | A1 | 3/2017 |
| EP | 3892617 | A1 | 10/2021 |
| FR | 2795073 | A1 | 12/2000 |
| JP | 2013-515688 | A | 5/2013 |
| WO | 93-07138 | A1 | 4/1993 |
| WO | 93-14080 | A1 | 7/1993 |
| WO | 2014-151005 | A1 | 9/2014 |
| WO | 2015-036560 | A1 | 3/2015 |
| WO | 2016-033100 | A1 | 3/2016 |
| WO | 2018-213777 | A1 | 11/2018 |
| WO | 2020-116296 | A1 | 6/2020 |

OTHER PUBLICATIONS

Extended European Search Report issued in corresponding European Patent Application No. 20918156.9 dated Nov. 8, 2023 (12 Pages).
Office Action issued in corresponding Chinese Patent Application No. 202080094911.9 dated Nov. 1, 2023, with English translation (14 Pages).
Inouye Et Al., "A Facile One-pot Preparation of 2-Methyl-and 2-Phenyl-4-fluoro-5-trifluoromethyl-6-methoxypyrimidine from Methyl Z-hydryl-2-(P-methyl)-F-propyl Ether" Journal of Fluorine Chemistry, vol. 7, 1985, pp. 231-236.
Office Action issued in corresponding Indian Patent Application No. 202237045705 dated Feb. 16, 2023, with English translation (6 Pages).

(Continued)

*Primary Examiner* — John S Kenyon
(74) *Attorney, Agent, or Firm* — Harness, Dickey & Pierce, P.L.C.

(57) ABSTRACT

A fluorine-containing pyrimidine compound represented by the following formula (1):

(1)

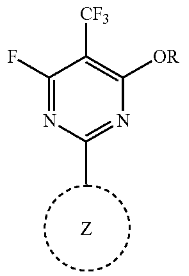

wherein in the general formula (1) above, R represents a hydrocarbon group having 1 to 12 carbon atoms, and a ring Z represents a fused heterocyclic ring containing a heteroatom.

11 Claims, No Drawings

(56) References Cited

OTHER PUBLICATIONS

Notice of Reasons for Refusal issued in corresponding Japanese Application No. 2022-500244 dated May 16, 2023, with English translation (7 Pages).

Zhang, Pei-Zhi et al., "Direct regioselective C—H trifluoromethylation of pyrimidinones and pyridinones", Tetrahedron, Jun. 9, 2016, vol. 72, Issue 23, pp. 3250-3255, Abstract (3 pages).

Yang, Bin et al., "Visible-Light Photoredox Decarboxylation of Perfluoroarene Iodine(III) Trifluoroacetates for C—H Trifluoromethylation of (Hetero)arenes", ACS Catalysis, Mar. 1, 2018, vol. 8, Issue 4, pp. 2839-2843, Abstract (1 page).

Ouyang, Yao et al., "Trifluoromethanesulfonic Anhydride as a Low-Cost and Versatile Trifluoromethylation Reagent", Angewandte Chemie International Edition, Apr. 19, 2018, vol. 57, Issue 23, pp. 6926-6929, Abstract (3 pages).

International Search Report for corresponding International Application No. PCT/JP2020/046908, mailed Feb. 2, 2021, with English translation (5 Pages).

International Preliminary Report on Patentability for corresponding International Application No. PCT/JP2020/046908 dated Feb. 2, 2021, with English translation (8 Pages).

Written Opinion for corresponding International Application No. PCT/JP2020/046908 dated Feb. 2, 2021, with English translation (7 Pages).

Notice of Reasons for Refusal issued in corresponding Japanese Application No. 2022-500244 dated Jul. 11, 2023, with English translation (4 Pages).

Office Action issued in corresponding European Patent Application No. 20918156.9 dated Dec. 17, 2024 (5 Pages).

FLUORINE-CONTAINING PYRIMIDINE COMPOUND AND PRODUCTION METHOD THEREFOR

CROSS REFERENCE TO RELATED APPLICATIONS

The present application is a national stage application of International Patent Application No. PCT/JP2020/046908 filed on Dec. 16, 2020, which claims the benefit of Japanese Patent Application No. 2020-021837, filed on Feb. 12, 2020. The contents of these applications are incorporated herein by reference in their entirety.

BACKGROUND

Technical Field

The present disclosure relates to a fluorine-containing pyrimidine compound and a production method therefor.

Related Art

Conventionally, fluorine-containing pyrimidine compounds have been reported to have various biological activities. Among them, a compound having a fused heterocyclic ring containing a heteroatom as a substituent at the 2-position of a pyrimidine ring is expected to be used in the fields of medicine and agrochemicals.

More specifically, WO2016/033100 reports that a compound having a benzotriazole ring as a substituent at the 2-position of the pyrimidine ring has a ULK1 inhibitory activity.

Moreover, WO2014/151005 reports that a compound having an indole ring as a substituent at the 2-position of the pyrimidine ring has a herbicidal activity against red-root amaranth and sunflower.

Further, WO2015/036560 reports that a compound having a quinoline ring as a substituent at the 2-position of the pyrimidine ring is effective in the treatment and prevention of cardiovascular and kidney diseases.

Therefore, modification of the 4-, 5-, and 6-positions of the pyrimidine ring has been of interest with an expectation of further improving the activity of fluorine-containing pyrimidine compounds. On the other hand, a synthetic method for a pyrimidine compound having a trifluoromethyl group at the 5-position of the pyrimidine ring and substituents at the 4- and 6-positions of the pyrimidine ring is disclosed in Tetrahedron, Vol. 72, 2016, pp. 3250 to 3255, ACS Catalysis, Vol. 8, 2018, pp. 2839 to 2843, and Angewandte Chemie International Edition, Vol. 57, 2018, pp. 6926 to 6929. More specifically, Tetrahedron, Vol. 72, 2016, pp. 3250 to 3255 reports a synthetic method using sodium trifluoromethanesulfinate (Langlois reagent), ACS Catalysis, Vol. 8, 2018, pp. 2839 to 2843 reports a synthetic method using a trifluoroacetic acid derivative, and Angewandte Chemie International Edition, Vol. 57, 2018, pp. 6926 to 6929 reports a synthetic method using anhydrous trifluoromethanesulfonic acid.

Technical Problem

However, production of a fluorine-containing pyrimidine compound having a fluorine-containing substituent at the 5-position of a pyrimidine ring, a fused heterocyclic ring containing a heteroatom as a substituent at the 2-position of a pyrimidine ring, and substituents at the 4- and 6-positions of a pyrimidine ring, has been conventionally difficult in terms of reactivity and selectivity thereof, and such a fluorine-containing pyrimidine compound has not been reported. The fluorine-containing pyrimidine compound is expected to have various biological activities.

On the other hand, the production method reported in Tetrahedron, Vol. 72, 2016, pp. 3250 to 3255 was required to significantly improve introduction efficiency of a trifluoromethyl group for a substrate with multiple heterocyclic rings, such as a pyrimidine compound substituted with a heterocyclic ring, since it has low regioselectivity upon introduction of the trifluoromethyl group. Moreover, it was necessary to use three times an amount of Langlois reagent as a trifluoromethylating agent for the substrate as well as separately three times an amount of manganese (III) acetate hydrate that is harmful as an oxidant, for the substrate.

By further modifying and derivatizing the compounds obtained by the production methods reported in ACS Catalysis, Vol. 8, 2018, pp. 2839 to 2843 and Angewandte Chemie International Edition, Vol. 57, 2018, pp. 6926 to 6929, they are considered to be converted into fluorine-containing pyrimidine compounds having a fused heterocyclic ring containing a heteroatom as a substituent at the 2-position of the pyrimidine ring. However, complication and a reduction of efficiency due to an increase in the number of process steps might have been inevitable, or the production of the fluorine-containing pyrimidine compound itself might have been difficult. Moreover, the production methods of ACS Catalysis, Vol. 8, 2018, pp. 2839 to 2843 and Angewandte Chemie International Edition, Vol. 57, 2018, pp. 6926 to 6929 required light irradiation in the presence of a ruthenium complex catalyst. Furthermore, the production method of ACS Catalysis, Vol. 8, 2018, pp. 2839 to 2843 required two point five to three times an amount of trifluoromethylating agent for the substrate, and the production method of Angewandte Chemie International Edition, Vol. 57, 2018, pp. 6926 to 6929 required three times an amount of trifluoromethylating agent for the substrate.

Therefore, establishment of a novel fluorine-containing pyrimidine compound having substituents at the 4- and 6-positions of the pyrimidine ring and a fused heterocyclic ring containing a heteroatom at the 2-position of the pyrimidine ring as a substituent and the production method therefor has been desired. Then, the present inventors have found that reaction of a specific raw material by a specific method enables to introduce a group composed of a fused heterocyclic ring containing a heteroatom into the 2-position between two nitrogen atoms on the pyrimidine ring, and thus have completed the present disclosure. Namely, the present disclosure provides a novel fluorine-containing pyrimidine compound having a fluorine-containing substituent at the 5-position, substituents at the 4- and 6-positions, and a fused heterocyclic ring containing a heteroatom as a substituent at the 2-position, which has not previously been known, and a production method capable of easily producing the fluorine-containing pyrimidine compound.

SUMMARY

The configuration of gist of the present disclosure is as follows.

[1] A fluorine-containing pyrimidine compound represented by the following general formula (1):

[Formula 1]

(1)

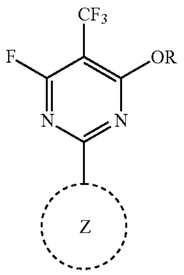

wherein in the general formula (1), R represents a hydrocarbon group having 1 to 12 carbon atoms, and a ring Z represents a fused heterocyclic ring containing a heteroatom.

[2] The fluorine-containing pyrimidine compound according to [1], wherein the heteroatom is at least one type of atom selected from the group consisting of a nitrogen atom, an oxygen atom, and a sulfur atom, and the fused heterocyclic ring is an aromatic fused heterocyclic ring.

[3] The fluorine-containing pyrimidine compound according to [1], wherein the number of π electrons constituting the ring Z is 10, 14, or 18.

[4] A method for producing a fluorine-containing pyrimidine compound, comprising reacting a fluoroisobutylene derivative represented by the following general formula (2) with a compound represented by the following general formula (3) or a salt thereof to obtain a fluorine-containing pyrimidine compound represented by the following general formula (1):

[Formula 2]

(2)

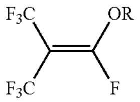

(3)

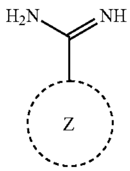

-continued (1)

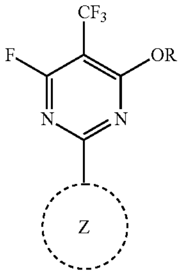

wherein in the general formulae (1) to (3), R represents a hydrocarbon group having 1 to 12 carbon atoms, and a ring Z represents a fused heterocyclic ring containing a heteroatom.

[5] A method for producing a fluorine-containing pyrimidine compound, comprising reacting a fluoroisobutane derivative represented by the following general formula (4) with a compound represented by the following general formula (3) or a salt thereof to obtain a fluorine-containing pyrimidine compound represented by the following general formula (1):

[Formula 3]

(4)

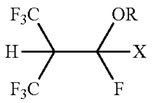

(3)

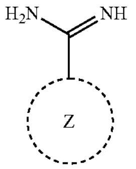

(1)

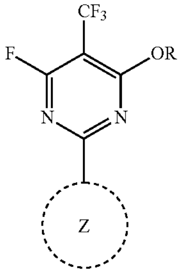

wherein in the general formulae (1), (3) and (4), R represents a hydrocarbon group having 1 to 12 carbon atoms; X represents a halogen atom, $-OA^1$, $-SO_mA^1$ where m is an integer of 0 to 3, or $-NA^1A^2$, wherein $A^1$ and $A^2$ each independently represent a hydrogen atom or a hydrocarbon group having 1 to 10 carbon atoms; and a ring Z represents a fused heterocyclic ring containing a heteroatom.

[6] The method for producing a fluorine-containing pyrimidine compound according to [4], wherein the heteroatom is at least one type of atom selected from the group consisting of a nitrogen atom, an oxygen atom, and a sulfur atom, and the fused heterocyclic ring is an aromatic fused heterocyclic ring.

[7] The method for producing a fluorine-containing pyrimidine compound according to [4], wherein the number of π electrons constituting the ring Z is 10, 14, or 18.

[8] The fluorine-containing pyrimidine compound according to [2], wherein the number of π electrons constituting the ring Z is 10, 14, or 18.

[9] The method for producing a fluorine-containing pyrimidine compound according to [5], wherein the heteroatom is at least one type of atom selected from the group consisting of a nitrogen atom, an oxygen atom, and a sulfur atom, and the fused heterocyclic ring is an aromatic fused heterocyclic ring.

[10] The method for producing a fluorine-containing pyrimidine compound according to [5], wherein the number of π electrons constituting the ring Z is 10, 14, or 18.

[11] The method for producing a fluorine-containing pyrimidine compound according to [6], wherein the number of π electrons constituting the ring Z is 10, 14, or 18.

Effects of Disclosure

A novel fluorine-containing pyrimidine compound having a fluorine-containing substituent at the 5-position, substituents at the 4- and 6-positions, and a fused heterocyclic ring containing a heteroatom as a substituent at the 2-position, and a production method capable of easily producing the fluorine-containing pyrimidine compound can be provided.

DETAILED DESCRIPTION (Fluorine-Containing Pyrimidine Compound)

The fluorine-containing pyrimidine compound in one embodiment is represented by the following general formula (1):

[Formula 4]

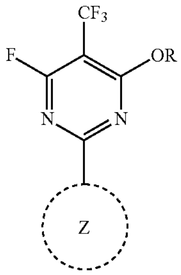

(1)

wherein in general formula (1) above, R represents a hydrocarbon group having 1 to 12 carbon atoms, and a ring Z represents a fused heterocyclic ring containing a heteroatom.

R is not particularly limited as long as it is a hydrocarbon group having 1 to 12 carbon atoms and is composed of a carbon atom and a hydrogen atom, and includes a chain hydrocarbon group, an aromatic hydrocarbon group, an alicyclic hydrocarbon group, and the like. The chain hydrocarbon group is not particularly limited as long as the total number of carbon atoms is 1 to 12 and may be a branched chain hydrocarbon group or an unbranched chain hydrocarbon group. The aromatic hydrocarbon group is not particularly limited as long as the total number of carbon atoms is 6 to 12 and may be an aromatic hydrocarbon group having a substituent or an aromatic hydrocarbon group having no substituent. Moreover, the aromatic hydrocarbon group may also have a fused polycyclic structure. The alicyclic hydrocarbon group is not particularly limited as long as the total number of carbon atoms is 3 to 12 and may be an alicyclic hydrocarbon group having a substituent or an alicyclic hydrocarbon group having no substituent. The alicyclic hydrocarbon group may also have a bridged ring structure.

Examples of the chain hydrocarbon group include alkyl groups such as a methyl group, an ethyl group, a n-propyl group, an i-propyl group, a n-butyl group, an i-butyl group, a sec-butyl group, a t-butyl group, a pentyl group, a hexyl group, a heptyl group, an octyl group, a nonyl group, a decyl group, an undecyl group, and a dodecyl group;

alkenyl groups such as an ethenyl group, a propenyl group, a butenyl group, a pentenyl group, a hexenyl group, a heptenyl group, an octenyl group, a nonenyl group, a decenyl group, an undecenyl group, and a dodecenyl group; and alkynyl groups such as an ethynyl group, a propynyl group, a butynyl group, a pentynyl group, a hexynyl group, a heptynyl group, an octynyl group, a nonynyl group, a decynyl group, an undecynyl group, and a dodecynyl group.

Examples of the aromatic hydrocarbon group include a phenyl group and a naphthyl group.

Examples of the alicyclic hydrocarbon group include a saturated or unsaturated cyclic hydrocarbon group, and examples of the cyclic hydrocarbon group include a cyclopropyl group, a cyclobutyl group, a cyclohexyl group, a cyclopentyl group, an adamantyl group, and a norbornyl group.

R is preferably an alkyl group having 1 to 10 carbon atoms. R being an alkyl group having 1 to 10 carbon atoms can easily prepare the fluoroisobutylene derivative of the general formula (2) and the fluoroisobutane derivative of the general formula (4), which are raw materials of the fluorine-containing pyrimidine compound.

The heteroatom is preferably at least one type of atom selected from the group consisting of a nitrogen atom, an oxygen atom, and a sulfur atom. The number of heteroatoms that are ring atoms constituting the fused heterocyclic ring is not particularly limited, and for example, the number of heteroatoms can be 1, 2, 3, or 4. The type of heteroatom that is a ring atom constituting the fused heterocyclic ring is not particularly limited as long as it is at least one type of atom selected from the group consisting of a nitrogen atom, an oxygen atom, and a sulfur atom, and the heteroatom may be one type, two types, or three types. When the ring atom constituting the fused heterocyclic ring is of one type, a nitrogen atom, an oxygen atom, or a sulfur atom may be used as the ring atom. When the ring atom constituting the fused heterocyclic ring is of two types, a nitrogen atom and a sulfur atom, a nitrogen atom and an oxygen atom, or an oxygen atom and a sulfur atom may be used as the ring atoms. When the ring atom constituting the fused heterocyclic ring is of three types, a nitrogen atom, a sulfur atom, and an oxygen atom can be used as the ring atoms. The number of ring atoms constituting the fused heterocyclic ring is not particularly limited, and for example, the number of ring atoms can be 5, 6, 8, 10, 13, 14, 16, 18, 20, or 22. The number of rings of the fused heterocyclic ring is not particularly limited as long as it has a polycyclic structure of two or more rings, and for example, the number of rings can be 2, 3, 4, or 5. The fused heterocyclic ring constituting the ring Z may be an aromatic fused heterocyclic ring or an alicyclic fused heterocyclic ring, and the fused heterocyclic ring constituting the ring Z is preferably the aromatic fused heterocyclic ring, and the number of π electrons constituting the ring Z is more preferably 10, 14, or 18. The ring Z satisfying these conditions can improve affinity for receptors with a polycyclic aromatic hydrocarbon as a ligand while controlling the kinetics. This thereby enables to impart more effective biological activity to the fluorine-containing pyrimidine compound.

The group composed of the ring Z is not particularly limited as long as it is a group composed of the fused heterocyclic ring containing a heteroatom. For example, the group composed of the ring Z includes a fused heterocyclic ring in which the number of ring atoms is 9 or 10 and which contains one, two, three, or four nitrogen atoms as heteroatoms (ring atoms) and which is composed of two rings. Moreover, the group composed of the ring Z includes, for example, a fused heterocyclic ring in which the number of ring atoms is 13 and which contains one, two, three, or four heteroatoms (ring atoms) and which is composed of three rings. More specifically, the group composed of the ring Z includes a benzotriazole group, a methylindolyl group, an indolyl group, an isoindolyl group, a quinolyl group, an isoquinolyl group, a naphthyridyl group, a benzofuryl group, a pyrrolidyl group, an indolizinyl group, a benzothienyl group, an isobenzofuranyl group, a dibenzofuranyl group, a chromenyl group, an indazolyl group, a purinyl group, a pteridinyl group, a quinolizinyl group, a naphthyridinyl group, a quinoxalinyl group, a cinnolinyl group, a benzothiazolyl group, a benzisothiazolyl group, a quinazolinyl group, a phthalazinyl group, a benzoxazolyl group, a benzimidazolyl group, a pyridopyrimidinyl group, an isochromanyl group, a chromanyl group, an indolinyl group, an isoindolinyl group, a tetrahydroquinolyl group, a tetrahydroisoquinolyl group, a tetrahydroquinoxalinyl group, a dihydrophthaladinyl group, a carbazolyl group, a phenazinyl group, an acridinyl group, a phenanthridinyl group, a thiantrenyl group, a phenoxazinyl group, a phenothiazinyl group, and the like. The group composed of the ring Z is preferably a benzotriazole group, a methylindolyl group, a quinolyl group, a naphthyridyl group, a benzothiazolyl group, or a dibenzofuranyl group.

The fluorine-containing pyrimidine compound in one embodiment has a specific substituent (group composed of the fused heterocyclic ring containing a heteroatom) at the 2-position of the pyrimidine ring, and specific substituents (—OR, —$CF_3$, —F) on the 4-, 5-, and 6-positions of the pyrimidine ring, and thereby it can have an excellent effect from the viewpoint of structural expandability. In particular, desired biological activities (for example, hormone or enzyme inhibitory activity, control activity of harmful organisms) can be expected. For example, the control activity includes a control activity against rice blast fungus. The structure composed of the fused heterocyclic ring containing a heteroatom on the 2-position of the pyrimidine ring may or may not further have a substituent. The presence of the substituent of the fused heterocyclic ring containing a heteroatom can impart additional properties to the fluorine-containing pyrimidine compound of one embodiment. Moreover, the substituents on the 4- and 6-positions of the pyrimidine ring being different groups (—OR and —F) facilitates derivatization into an asymmetric structure, leading to expectation of potential use as an intermediate. More specifically, a fluorine-containing pyrimidine compound being reacted under acidic conditions to modify —OR enables to form a derivative. Moreover, a fluorine-containing pyrimidine compound being reacted under basic conditions to modify —F enables to form a derivative. The fluorine-containing pyrimidine compound of one embodiment is useful in the field of electronic materials such as organic semiconductors and liquid crystals.

(Method for Producing Fluorine-Containing Pyrimidine Compound)

The method for producing a fluorine-containing pyrimidine compound in one embodiment comprises (a) reacting a fluoroisobutylene derivative represented by the following general formula (2) with a compound represented by the following general formula (3) or a salt thereof to obtain a fluorine-containing pyrimidine compound represented by the following general formula (1):

[Formula 5]

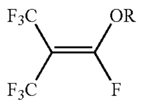

(2)

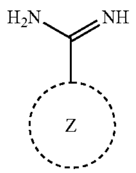

(3)

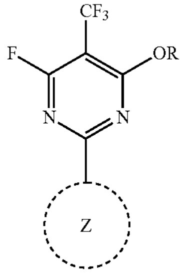

(1)

wherein in the general formulae (1) to (3) above, R represents a hydrocarbon group having 1 to 12 carbon atoms, and a ring Z represents a fused heterocyclic ring containing a heteroatom.

The reaction of step (a) above between the fluoroisobutylene derivative represented by the general formula (2) and the compound represented by the general formula (3) is represented by the following reaction formula (A).

[Formula 6]

(A)

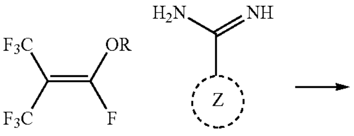

(2) (3)

-continued

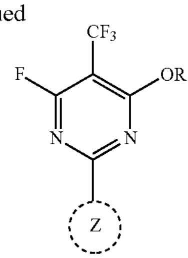

+ 3HF (1)

In reaction formula (A) above, the compounds of the general formula (3) each may be in a form of salt. The form of salt includes, for example, a form of at least one of the amino moiety (—$NH_2$) and the imino moiety (=NH) constituting the amidino group of the compound of the general formula (3), being cationized to (—$NH_3^+$) and (=$NH_2^+$) to form a salt with the counterion. The counterion is not particularly limited as long as it is a monovalent anion, and includes, for example, halide ions such as $F^-$, $Cl^-$, $Br^-$, and $I^-$.

In the method for producing the fluorine-containing pyrimidine compound in one embodiment, for example, the reaction of step (a) above can be carried out in one step in the presence of the hydrogen halide scavenger. Therefore, the fluorine-containing pyrimidine compound of the general formula (1) above can be easily obtained. The reaction of step (a) above forms a cyclic pyrimidine structure between the fluoroisobutylene derivative and the amidino group of the compound of the general formula (3). At the 2-position of the pyrimidine structure, a group derived from the ring Z of the compound of the general formula (3) is located. Further, —OR, $CF_3$, and F derived from the fluoroisobutylene derivative are located at the 4-position, 5-position, and 6-position of the pyrimidine structure, respectively.

The hydrogen halide scavenger is a substance having a function of capturing hydrogen fluoride (HF) formed from a hydrogen atom derived from the amidino group in the compound of the general formula (3) in reaction formula (A) above, and a fluorine atom derived from the fluoroisobutylene derivative of the general formula (2). The hydrogen halide scavenger that is sodium hydroxide, potassium hydroxide, calcium hydroxide, sodium carbonate, potassium carbonate, sodium fluoride and potassium fluoride, and organic nitrogen derivatives such as pyridine, triethylamine, diisopropylethylamine, diazabicyclo nonane and diazabicyclo undecene, methyl triazabicyclodecene, and diazabicyclo octane can be used.

Moreover, the step of obtaining the fluorine-containing pyrimidine compound of (A) above is preferably carried out in the presence of a fluoride ion scavenger. The fluoroisobutylene derivative represented by the general formula (2) is preferably reacted with the compound represented by the general formula (3) or a salt thereof in the presence of the fluoride ion scavenger. The reaction in (A) above in the presence of the fluoride ion scavenger allows the reaction to be efficiently carried out to obtain the fluorine-containing pyrimidine compound in a high yield. The fluoride ion scavenger includes a salt of a cation such as lithium, sodium, magnesium, potassium, calcium, or tetramethylammonium, and an anion such as trifluoroacetic acid, heptafluorobutyric acid, methanesulfonic acid, ethanesulfonic acid, benzenesulfonic acid, toluenesulfonic acid, trifluoromethanesulfonic acid, nonafluorobutanesulfonic acid, bis(trifluoromethanesulfonyl)imide, bis(nonafluorobutanesulfonyl)imide, N,N-hexafluoropropane-1,3-disulfonylimide, tetraphenyl-boric acid, tetrakis[3,5-bis(trifluoromethyl)phenyl]boric acid, or tetrakis(pentafluorophenyl)boric acid. Among them, the use of the potassium salt or the sodium salt using potassium or sodium as the cation is preferred, and the use of the sodium salt using sodium as the cation is more preferred. It is conjectured that a cation derived from the fluoride ion scavenger captures fluorine ions free from the fluoroisobutylene derivative represented by the general formula (2) during reaction, allowing a salt having low solubility for an organic solvent to precipitate therein to promote a reaction, and enabling to obtain the fluorine-containing pyrimidine compound represented by the general formula (1) above in a high yield.

A reaction temperature upon reaction of step (a) above is preferably 0 to 100° C., more preferably 5 to 50° C., and still more preferably 10 to 20° C. A reaction time upon reaction of step (a) above is preferably 1 to 48 hours, more preferably 2 to 36 hours, and still more preferably 4 to 24 hours.

A solvent used in the reaction of step (a) above includes aprotic polar solvents such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide, and sulfolane, or two-phase solvents of a protonic polar solvent such as water, and water-insoluble solvents such as dichloromethane, toluene, and diethyl ether. Moreover, as a catalyst for the reaction of step (a) above, a quaternary ammonium halide such as benzyltriethylammonium chloride, a quaternary phosphonium halide, and crown ether can be used.

The method for producing a fluorine-containing pyrimidine compound of another embodiment has (b) reacting a fluoroisobutane derivative represented by the following general formula (4) with a compound represented by the following general formula (3) or a salt thereof to obtain a fluorine-containing pyrimidine compound represented by the following general formula (1):

[Formula 7]

(4)

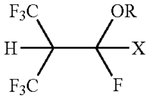

(3)

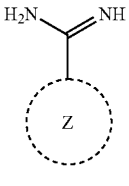

(1)

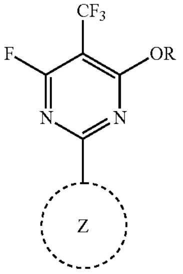

wherein in the general formulae (1), (3), and (4) above, R represents a hydrocarbon group having 1 to 12 carbon atoms; X represents a halogen atom, —$OA^1$, —$SO_mA^1$ where m is an integer of 0 to 3, or —$NA^1A^2$, wherein $A^1$ and $A^2$ each independently represent a hydrogen atom or a hydrocarbon group having 1 to 10 carbon atoms; and a ring Z represents a fused heterocyclic ring containing a heteroatom.

$A^1$ included in X that is —$OA^1$ and —$SO_mA^1$ where m is an integer of 0 to 3 represents a hydrogen atom or a hydrocarbon group having 1 to 10 carbon atoms. $A^1$ and $A^2$ included in X that is —$NA^1A^2$ each independently represent a hydrogen atom or a hydrocarbon group having 1 to 10 carbon atoms. When $A^1$ and $A^2$ represent hydrocarbon groups having 1 to 10 carbon atoms, for example, they can be hydrocarbon groups having 1 to 10 carbon atoms in R above.

The reaction of step (b) above between the fluoroisobutane derivative represented by the general formula (4) and the compound represented by the general formula (3) is represented by the following reaction formula (B).

[Formula 8]

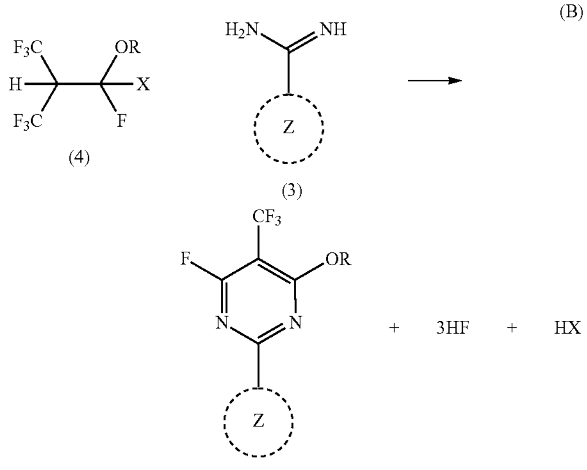

(B)

(4) (3) (1)

In reaction formula (B) above, the compound of the general formula (3) each may be in a form of salt. The form of salt includes, for example, a form of at least one of the amino moiety (—$NH_2$) and the imino moiety (═NH) constituting the amidino group of the compound of the general formula (3), being cationized to (—$NH_3^+$) and (═$NH_2^+$) to form a salt with the counterion. The counterion is not particularly limited as long as it is a monovalent anion, and includes, for example, halide ions such as $F^-$, $Cl^-$, $Br^-$, and $I^-$.

In the method for producing the fluorine-containing pyrimidine compound of another embodiment, for example, reaction (B) above can be carried out in one step. Therefore, the fluorine-containing pyrimidine compound of the general formula (1) above can be easily obtained. The reaction of step (b) above forms a cyclic pyrimidine structure between the fluoroisobutane derivative and the amidino group of the compound of the general formula (3). At the 2-position of the pyrimidine structure, a group derived from the ring Z of the compound of the general formula (3) is located. Further, —OR, $CF_3$, and F derived from the fluoroisobutane derivative are located at the 4-position, 5-position, and 6-position of the pyrimidine structure, respectively.

A reaction temperature upon reaction of step (b) above is preferably 0 to 100° C., more preferably 5 to 50° C., and still more preferably 10 to 20° C. A reaction time upon reaction of step (b) above is preferably 1 to 48 hours, more preferably 3 to 36 hours, and still more preferably 4 to 24 hours. In the reaction of step (b) above, the same hydrogen halide scavenger as in step (a) above can be used.

A solvent used in the reaction of step (b) above includes aprotic polar solvents such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide, and sulfolane, or two-phase solvents of a protonic polar solvent such as water, and water-insoluble solvents such as dichloromethane, toluene, and diethyl ether. Moreover, as a catalyst for reaction of step (b) above, a quaternary ammonium halide such as benzyltriethylammonium chloride, a quaternary phosphonium halide, and crown ether can be used.

In steps (a) and (b) above, the heteroatom is preferably at least one type of atom selected from the group consisting of a nitrogen atom, an oxygen atom, and a sulfur atom. Moreover, the fused heterocyclic ring constituting the ring Z is preferably the aromatic fused heterocyclic ring, and the number of π electrons constituting the ring Z is more preferably 10, 14, or 18.

In steps (a) and (b) above, R in the general formulae (1), (2), and (4) preferably represents an alkyl group having 1 to 10 carbon atoms. Moreover, in steps (a) and (b) above, the group composed of the ring Z in the general formulae (1) and (3) is not particularly limited as long as it is a group composed of the fused heterocyclic ring containing a heteroatom. For example, the group composed of the ring Z includes a fused heterocyclic ring in which the number of ring atoms is 9 or 10 and which contains one, two, three, or four nitrogen atoms as heteroatoms (ring atoms) and which is composed of two rings. Moreover, the group composed of the ring Z includes, for example, a fused heterocyclic ring in which the number of ring atoms of 13 and which contains one, two, three, or four heteroatoms (ring atoms) and which is composed of three rings. More specifically, the group composed of the ring Z includes a benzotriazole group, a methylindolyl group, an indolyl group, an isoindolyl group, a quinolyl group, an isoquinolyl group, a naphthyridyl group, a benzofuryl group, a pyrrolidyl group, an indolizinyl group, a benzothienyl group, an isobenzofuranyl group, a dibenzofuranyl group, a chromenyl group, an indazolyl group, a purinyl group, a pteridinyl group, a quinolizinyl group, a naphthyridinyl group, a quinoxalinyl group, a cinnolinyl group, a benzothiazolyl group, a benzisothiazolyl group, a quinazolinyl group, a phthalazinyl group, a benzoxazolyl group, a benzimidazolyl group, a pyridopyrimidinyl group, an isochromanyl group, a chromanyl group, an indolinyl group, an isoindolinyl group, a tetrahydroquinolyl group, a tetrahydroisoquinolyl group, a tetrahydroquinoxalinyl group, a dihydrophthaladinyl group, a carbazolyl group, a phenazinyl group, an acridinyl group, a phenanthridinyl group, a thiantrenyl group, a phenoxazinyl group, a phenothiazinyl group, and the like. The group composed of the ring Z is preferably a benzotriazole group, a methylindolyl group, a quinolyl group, a naphthyridyl group, a benzothiazolyl group, or a dibenzofuranyl group.

Although embodiments of the present disclosure have been described above, the present disclosure is not limited to the aforementioned embodiments, and includes all aspects included in the concept and claims of the present disclosure and can be modified within the scope of the present disclosure in various embodiments.

EXAMPLES

Next, in order to further clarify the effect of the present disclosure, Examples will be described, but the present disclosure is not limited to these Examples.

Example 1

Production of 2-(1-benzotriazolyl)-6-fluoro-4-methoxy-5-trifluoromethylpyrimidine Under ice-water cooling, 6.7 g (20 mmol) of 1-amidinobenzotriazole toluenesulfonate, 25.5 g (80 mmol) of potassium bis(trifluoromethanesulfonyl)imide, and 4.9 g (23 mmol) of 1,3,3,3-tetrafluoro-1-methoxy-2-(trifluoromethyl)-1-propene were added to 35 g of tetrahydrofuran. Subsequently, a mixed solution of 13.4 g (104 mmol) of diisopropylethylamine and 15 g of tetrahydrofuran was added dropwise such that the internal temperature did not exceed 10° C. and was raised to room temperature. After about 24 hours, a column purification of the content was performed to obtain 0.13 g of a compound represented by the following formula (5) (chemical formula: $C_{12}H_7F_4N_5O$, molecular weight: 313.22 g/mol). The isolated yield of the compound represented by the following formula (5) was 2%.

[Formula 9]

(5)

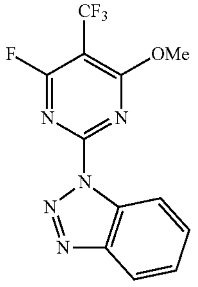

The analysis results of the obtained compound are as follows.

Mass Spectrum (APCI, m/z): 313 ($[M]^+$)

$^1$H-NMR (400 MHz, $CDCl_3$) δ ppm: 8.49 (d, 1H), 8.21 (d, 1H), 7.72 (t, 1H), 7.56 (t, 1H), 4.39 (s, 3H)

$^{19}$F-NMR (400 MHz, $C_6F_6$) δ ppm: −57.8 (m, 1F), −58.6 (d, 3F)

Example 2

Production of 6-fluoro-2-(4-(1-methyl)indolyl)-4-methoxy-5-trifluoromethylpyrimidine Under ice-water cooling, 4.2 g (20 mmol) of 4-amidino-1-methylindole hydrochloride and 4.9 g (23 mmol) of 1,3,3,3-tetrafluoro-1-methoxy-2-(trifluoromethyl)-1-propene were added to 10 g of acetonitrile. Subsequently, a mixed solution of 13.4 g (104 mmol) of diisopropylethylamine and 15 g of acetonitrile was added dropwise such that the internal temperature did not exceed 10° C. and was raised to room temperature. After about 16 hours, a column purification of the content was performed to obtain 1.1 g of a compound represented by the following formula (6) (chemical formula: $C_{15}H_{11}F_4N_3O$, molecular weight: 325.27 g/mol). The isolated yield of the compound represented by the following formula (6) was 17%.

[Formula 10]

(6)

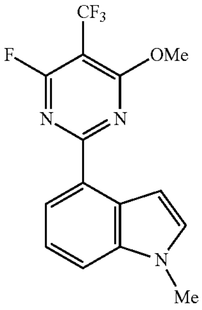

The analysis results of the obtained compound are as follows.

Mass Spectrum (APCI, m/z): 325 ($[M]^+$)

$^1$H-NMR (400 MHz, $CDCl_3$) δ ppm: 8.32 (dd, 1H), 7.53 (dd, 1H), 7.46 (t, 1H), 7.31 (ddd, 1H), 7.23 (dd, 1H), 4.29 (s, 3H), 3.86 (s, 3H)

$^{19}$F-NMR (400 MHz, $C_6F_6$) δ ppm: −58.2 (d, 3F), −61.2 (dd, 1F)

Example 3

Production of 6-fluoro-4-methoxy-2-(2-quinolino)-5-trifluoromethylpyrimidine Under ice-water cooling, 4.2 g (20 mmol) of 2-amidinoquinoline hydrochloride and 4.9 g (23 mmol) of 1,3,3,3-tetrafluoro-1-methoxy-2-(trifluoromethyl)-1-propene were added to 10 g of acetonitrile. Subsequently, a mixed solution of 13.4 g (104 mmol) of diisopropylethylamine and 15 g of acetonitrile was added dropwise such that the internal temperature did not exceed 10° C. and was raised to room temperature. After about 16 hours, a column purification of the content was performed to obtain 2.1 g of a compound represented by the following formula (7) (chemical formula: $C_{15}H_9F_4N_3O$, molecular weight: 323.25 g/mol). The isolated yield of the compound represented by the following formula (7) was 33%.

[Formula 11]

(7)

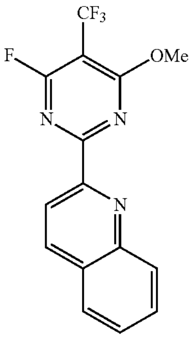

The analysis results of the obtained compound are as follows.

Mass Spectrum (APCI, m/z): 323 ([M]$^+$)

$^1$H-NMR (400 MHz, $CDCl_3$) δ ppm: 8.55 (d, 1H), 8.36 (dd, 2H), 7.90 (d, 1H), 7.80 (ddd, 1H), 7.65 (ddd, 1H), 4.33 (s, 3H)

$^{19}$F-NMR (400 MHz, $C_6F_6$) δ ppm: −58.7 (d, 3F), −59.3 (dd, 3F)

Example 4

Production of 6-fluoro-4-methoxy-2-(2-(1,6-naphthyridyl))-5-trifluoromethylpyrimidine Under ice-water cooling, 4.2 g (20 mmol) of 2-amidino-1,6-naphthyridine hydrochloride and 4.9 g (23 mmol) of 1,3,3,3-tetrafluoro-1-methoxy-2-(trifluoromethyl)-1-propene were added to 10 g of acetonitrile. Subsequently, a mixed solution of 13.4 g (104 mmol) of diisopropylethylamine and 15 g of acetonitrile was added dropwise such that the internal temperature did not exceed 10° C. and was raised to room temperature. After about 16 hours, a column purification of the content was performed to obtain 0.4 g of a compound represented by the following formula (8) (chemical formula: $C_{14}H_8F_4N_{40}$, molecular weight: 324.24 g/mol). The isolated yield of the compound represented by the following formula (8) was 6%.

[Formula 12]

(8)

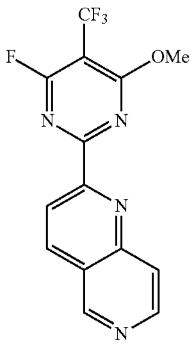

The analysis results of the obtained compound are as follows.

Mass Spectrum (APCI, m/z): 324 ([M]$^+$)

$^1$H-NMR (400 MHz, $CDCl_3$) δ ppm: 9.42 (d, 1H), 8.88 (m, 1H), 8.70 (m, 1H), 8.54 (dd, 1H), 8.20 (dd, 1H), 4.38 (m, 3H)

$^{19}$F-NMR (400 MHz, $C_6F_6$) δ ppm: −58.8 (m, 4F)

Example 5

Production of 2-(1-benzotriazolyl)-6-fluoro-4-methoxy-5-trifluoromethylpyrimidine by using 1,1,1,3,3-pentafluoro-3-methoxy-2-trifluoromethyl-propane instead of 1,3,3,3-tetrafluoro-1-methoxy-2-trifluoromethyl-1-propene of Example 1

Under ice-water cooling, 4.0 g (20 mmol) of 1-amidinobenzotriazole hydrochloride, 32 g (100 mmol) of potassium bis(trifluoromethanesulfonyl)imide, and 5.4 g (23 mmol) of 1,1,1,3,3-pentafluoro-3-methoxy-2-trifluoromethyl-propane were added to 35 g of tetrahydrofuran. Subsequently, a mixed solution of 16.8 g (130 mmol) of diisopropylethylamine and 15 g of tetrahydrofuran was added dropwise such that the internal temperature did not exceed 10° C. and was raised to room temperature. After about 24 hours, a column purification of the content was performed. The analysis results of the obtained compound were the same as those of the product of Example 1.

Example 6

Production of 6-fluoro-2-(4-(1-methyl)indolyl)-4-methoxy-5-trifluoromethylpyrimidine by using 1,1,1,3,3-pentafluoro-3-methoxy-2-trifluoromethyl-propane instead of 1,3,3,3-tetrafluoro-1-methoxy-2-trifluoromethyl-1-propene of Example 2

Under ice-water cooling, 4.2 g (20 mmol) of 4-amidino-1-methylindole hydrochloride and 5.4 g (23 mmol) of 1,1,1,3,3-pentafluoro-3-methoxy-2-trifluoromethyl-propane were added to 10 g of acetonitrile. Subsequently, a mixed solution of 16.8 g (130 mmol) of diisopropylethylamine and 15 g of acetonitrile was added dropwise such that the internal temperature did not exceed 10° C. and was raised to room temperature. After about 16 hours, a column purification of the content was performed. The analysis results of the obtained compound were the same as those of the product of Example 2.

Example 7

Production of 6-fluoro-4-methoxy-2-(2-quinolino)-5-trifluoromethylpyrimidine by using 1,1,1,3,3-pentafluoro-3-methoxy-2-trifluoromethyl-propane Instead of 1,3,3,3-tetrafluoro-1-methoxy-2-trifluoromethyl-1-propene of Example 3

Under ice-water cooling, 4.2 g (20 mmol) of 2-amidinoquinoline hydrochloride and 5.4 g (23 mmol) of 1,1,1,3,3-pentafluoro-3-methoxy-2-trifluoromethyl-propane were added to 10 g of acetonitrile. Subsequently, a mixed solution of 16.8 g (130 mmol) of diisopropylethylamine and 15 g of acetonitrile was added dropwise such that the internal temperature did not exceed 10° C. and was raised to room temperature. After about 16 hours, a column purification of the content was performed. The analysis results of the obtained compound were the same as those of the product of Example 3.

Example 8

Production of 6-fluoro-4-methoxy-2-(2-(1,6-naphthyridyl))-5-trifluoromethylpyrimidine by using 1,1,1,3,3-pentafluoro-3-methoxy-2-trifluoromethyl-propane instead of 1,3,3,3-tetrafluoro-1-methoxy-2-trifluoromethyl-1-propene of Example 4

Under ice-water cooling, 4.2 g (20 mmol) of 2-amidino-1,6-naphthyridine hydrochloride and 5.4 g (23 mmol) of 1,1,1,3,3-pentafluoro-3-methoxy-2-trifluoromethyl-propane were added to 10 g of acetonitrile. Subsequently, a mixed solution of 16.8 g (130 mmol) of diisopropylethylamine and 15 g of acetonitrile was added dropwise such that the internal temperature did not exceed 10° C. and was raised to room temperature. After about 16 hours, a column purification of the content was performed. The analysis results of the obtained compound were the same as those of the product of Example 4.

Example 9

Production of 2-(2-benzothiazolyl)-6-fluoro-4-methoxy-5-(trifluoromethyl)pyrimidine Under ice-water cooling, 0.5 g (2.3 mmol) of 2-amidinobenzothiazole hydrochloride and 0.6 g (2.7 mmol) of 1,3,3,3-tetrafluoro-1-methoxy-2-(trifluoromethyl)-1-propene were added to 10 g of acetonitrile. Subsequently, a mixed solution of 1.6 g (12 mmol) of diisopropylethylamine and 5 g of acetonitrile was added dropwise such that the internal temperature did not exceed 10° C. and was raised to room temperature. After about 16 hours, a column purification of the content was performed to obtain 0.2 g of 2-(2-benzothiazolyl)-6-fluoro-4-methoxy-5-(trifluoromethyl)pyrimidine represented by the following formula (9) (chemical formula: $C_{13}H_7F_4N_3OS$, molecular weight: 329.27 g/mol). The yield of the compound represented by the following formula (9) was 23%.

[Formula 13]

(9)

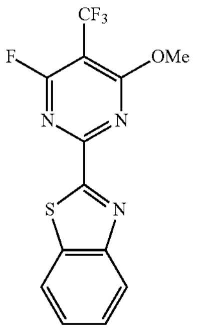

The analysis results of the target product obtained are as follows.

Mass Spectrum (APCI, m/z): 328.9 ($[M]^-$)

Example 10

Production of 2-(2-dibenzofuranyl)-6-fluoro-4-methoxy-5-(trifluoromethyl)pyrimidine Under ice-water cooling, 0.5 g (2 mmol) of 2-amidinodibenzofuran hydrochloride and 0.5 g (2.3 mmol) of 1,3,3,3-tetrafluoro-1-methoxy-2-(trifluoromethyl)-1-propene were added to 10 g of acetonitrile. Subsequently, a mixed solution of 1.4 g (11 mmol) of diisopropylethylamine and 5 g of acetonitrile was added dropwise such that the internal temperature did not exceed 10° C. and was raised to room temperature. After about 16 hours, a column purification of the content was performed to obtain 0.1 g of 2-(2-dibenzofuranyl)-6-fluoro-4-methoxy-5-(trifluoromethyl)pyrimidine represented by the following formula (10) (chemical formula: $C_{18}H_{10}F_4N_2O_2$, molecular weight: 362.28 g/mol). The yield of the compound represented by the following formula (10) was 18%.

[Formula 14]

(10)

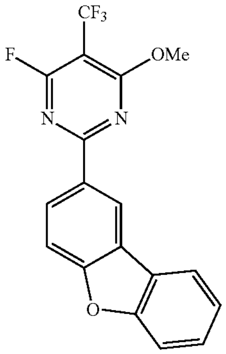

The analysis results of the target product obtained are as follows.

Mass Spectrum (APCI, m/z): 362.5 ($[M]^+$)

(Control Test for Rice Blast)

6-Fluoro-4-methoxy-2-(2-(1,6-naphthyridyl))-5-trifluoromethylpyrimidine prepared in Example 4 was dissolved in acetone to prepare an acetone solution with a concentration of 100,000 ppm of 6-fluoro-4-methoxy-2-(2-(1,6-naphthyridyl))-5-trifluoromethylpyrimidine. Sterilized water was added to 1 ml of this acetone solution to make 50 ml, to prepare a test solution having a concentration of 2,000 ppm. Next, sterilized water was added to 10 ml of the test solution having a concentration of 2,000 ppm to make 20 ml, to prepare a test solution having a concentration of 1,000 ppm. 1,000 μl of each of the test solution having a concentration of 2,000 ppm and the test solution having a concentration of 1,000 ppm was added dropwise to a separately prepared oatmeal culture medium and was air-dried. Subsequently, an 8 mm rice blast disc was placed such that flora contacted a treated surface of the oatmeal culture medium. Then, the oatmeal culture medium was allowed to stand still in a thermostatic room at 25° C. for 7 days, and an elongation length of hyphae was then investigated. The preventive value calculated according to expression (A) below is shown in Table 1 below.

Preventive value={(average of elongation lengths of hyphae without treatment−average of elongation lengths of hyphae with treatment)/average of elongation lengths of hyphae without treatment}×100 (A)

In expression (A) above, "without treatment" means that a solution prepared by diluting 1 ml of acetone with sterile water to make 50 ml as a test solution was added dropwise to the culture medium.

"With treatment" means that the test solution having a concentration of 2,000 ppm or the test solution having a concentration of 1,000 ppm was added dropwise to the culture medium.

TABLE 1

| Test solution concentration | Preventive value |
|---|---|
| 2000 ppm | 100 |
| 1000 ppm | 76 |

The results in Table 1 confirmed that 6-fluoro-4-methoxy-2-(2-(1,6-naphthyridyl))-5-trifluoromethylpyrimidine has a control activity against rice blast fungus.

The invention claimed is:

1. A fluorine-containing pyrimidine compound represented by the following general formula (1):

[Formula 1]

(1)

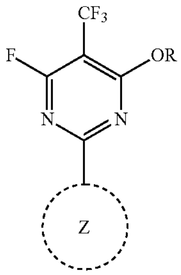

wherein in the general formula (1), R represents a hydrocarbon group having 1 to 12 carbon atoms, and a ring Z represents a fused heterocyclic ring containing a single heteroatom.

2. The fluorine-containing pyrimidine compound according to claim 1, wherein the single heteroatom is selected from the group consisting of a nitrogen atom, an oxygen atom, and a sulfur atom, and the fused heterocyclic ring is an aromatic fused heterocyclic ring.

3. The fluorine-containing pyrimidine compound according to claim 1, wherein the number of x electrons constituting the ring Z is 10, 14, or 18.

4. A method for producing a fluorine-containing pyrimidine compound, comprising reacting a fluoroisobutylene derivative represented by the following general formula (2) with a compound represented by the following general formula (3) or a salt thereof to obtain a fluorine-containing pyrimidine compound represented by the following general formula (1):

[Formula 2]

(2)

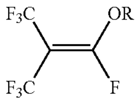

(3)

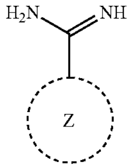

(1)

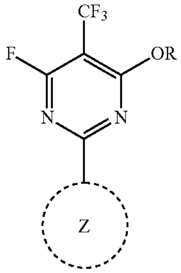

wherein in the general formulae (1) to (3), R represents a hydrocarbon group having 1 to 12 carbon atoms, and a ring Z represents a fused heterocyclic ring containing a single heteroatom.

5. A method for producing a fluorine-containing pyrimidine compound, comprising reacting a fluoroisobutane derivative represented by the following general formula (4) with a compound represented by the following general formula (3) or a salt thereof to obtain a fluorine-containing pyrimidine compound represented by the following general formula (1):

[Formula 3]

(4)

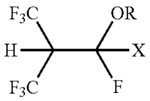

(3)

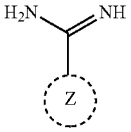

(1)

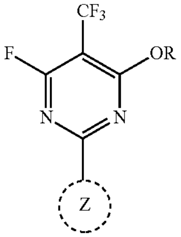

wherein in the general formulae (1), (3) and (4), R represents a hydrocarbon group having 1 to 12 carbon atoms; X represents a halogen atom, $—OA^1$, $—SO_mA^1$ where m is an integer of 0 to 3, or $—NA^1A^2$, wherein $A^1$ and $A^2$ each independently represent a hydrogen atom or a hydrocarbon group having 1 to 10 carbon atoms; and a ring Z represents a fused heterocyclic ring containing a single heteroatom.

6. The method for producing a fluorine-containing pyrimidine compound according to claim 4, wherein the single heteroatom is selected from the group consisting of a nitrogen atom, an oxygen atom, and a sulfur atom, and the fused heterocyclic ring is an aromatic fused heterocyclic ring.

7. The method for producing a fluorine-containing pyrimidine compound according to claim 4, wherein the number of x electrons constituting the ring Z is 10, 14, or 18.

8. The fluorine-containing pyrimidine compound according to claim 2, wherein the number of x electrons constituting the ring Z is 10, 14, or 18.

9. The method for producing a fluorine-containing pyrimidine compound according to claim 5, wherein the heteroatom is selected from the group consisting of a nitrogen atom, an oxygen atom, and a sulfur atom, and the fused heterocyclic ring is an aromatic fused heterocyclic ring.

10. The method for producing a fluorine-containing pyrimidine compound according to claim 5, wherein the number of x electrons constituting the ring Z is 10, 14, or 18.

11. The method for producing a fluorine-containing pyrimidine compound according to claim 6, wherein the number of x electrons constituting the ring Z is 10, 14, or 18.

* * * * *